US011295114B2

(12) United States Patent
Lee et al.

(10) Patent No.: US 11,295,114 B2
(45) Date of Patent: Apr. 5, 2022

(54) CREATION OF REPRESENTATIVE CONTENT BASED ON FACIAL ANALYSIS

(71) Applicant: Microsoft Technology Licensing, LLC, Redmond, WA (US)

(72) Inventors: David Lee, Redmond, WA (US); Chunkit Jacky Chan, Redmond, WA (US); Doug Ricard, Woodinville, WA (US); Stacia Scott, Bellingham, WA (US); Allison Light, Seattle, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 53 days.

(21) Appl. No.: 16/388,102

(22) Filed: Apr. 18, 2019

(65) Prior Publication Data

US 2019/0354748 A1  Nov. 21, 2019

Related U.S. Application Data

(63) Continuation of application No. 15/497,423, filed on Apr. 26, 2017, now Pat. No. 10,311,284, which is a
(Continued)

(51) Int. Cl.
*G06K 9/00* (2006.01)
*G06K 9/52* (2006.01)
*C07C 1/00* (2006.01)

(52) U.S. Cl.
CPC ....... *G06K 9/00268* (2013.01); *G06K 9/0061* (2013.01); *G06K 9/00221* (2013.01);
(Continued)

(58) Field of Classification Search
CPC ............. G06K 9/00617; G06K 9/4671; G06K 9/00288; G06K 9/00315; G06K 9/00281;
(Continued)

(56) References Cited

U.S. PATENT DOCUMENTS 5,060,170 A   10/1991  Bourgeois et al.
6,556,196 B1 *  4/2003  Blanz ................. G06K 9/00275
                                                  345/419
(Continued)

FOREIGN PATENT DOCUMENTS

CN   1337619 A   2/2002
CN   1649420 A   8/2005
(Continued)

OTHER PUBLICATIONS

"Summons to Attend Oral Proceedings Issued in European Patent Application No. 15728297.1", Mailed Date: Mar. 13, 2020, 8 Pages.
(Continued)

*Primary Examiner* — Yosef Kassa
(74) *Attorney, Agent, or Firm* — Watson Patents, PLC; Vladan M. Vasiljevic

(57) ABSTRACT

Technologies for analyzing various features detected in a face detected in an image. Such features may include at least the eyes, eyebrows, node, and mouth of a face. Such analyzing may include scoring aspects of these features. Such scores may be weighted. The analysis may be used to determine expressions and/or poses of the face, as well as indicate if the face is smiling, frowning, or neutral. An overall quality score for the face may also be determined and provided based on the aforementioned analysis as well as whether or not the face is near an edge of the image or cut-off in the image. Finally, a face signature may be determined that uniquely identifies the face, at least within the scope of the analyzed features. Such face signatures may be used to detect a similar face in other images.

20 Claims, 9 Drawing Sheets

Related U.S. Application Data continuation of application No. 14/264,012, filed on Apr. 28, 2014, now Pat. No. 9,639,742.

(52) U.S. Cl.
CPC ..... *G06K 9/00228* (2013.01); *G06K 9/00302* (2013.01); *G06K 9/52* (2013.01); *C07C 1/00* (2013.01)

(58) Field of Classification Search
CPC ...... G06K 9/00335; G06T 2207/30201; G06T 13/40
See application file for complete search history.

(56) References Cited

U.S. PATENT DOCUMENTS

| | | | |
|---|---|---|---|
| 6,606,096 B2* | 8/2003 | Wang | G06T 17/20 345/473 |
| 6,882,741 B2 | 4/2005 | Dobashi et al. | |
| 7,047,054 B2* | 5/2006 | Benni | A61B 5/14552 600/310 |
| 7,130,453 B2* | 10/2006 | Kondo | G06K 9/00604 382/117 |
| 7,233,684 B2* | 6/2007 | Fedorovskaya | G06K 9/6293 382/118 |
| 7,460,730 B2* | 12/2008 | Pal | G06K 9/32 382/284 |
| 7,599,519 B2* | 10/2009 | Yokouchi | G06K 9/00248 348/333.01 |
| 7,634,103 B2* | 12/2009 | Rubinstenn | H04N 5/23206 382/100 |
| 7,643,671 B2* | 1/2010 | Dong | G06K 9/00288 382/154 |
| 7,653,220 B2* | 1/2010 | Nishimori | G06T 11/00 382/118 |
| 7,756,302 B2* | 7/2010 | Matsuzaka | H04N 5/23293 382/118 |
| 7,881,479 B2 | 2/2011 | Asada | |
| 8,024,564 B2 | 9/2011 | Bassani et al. | |
| 8,031,775 B2* | 10/2011 | Luo | H04N 5/145 375/240.16 |
| 8,036,432 B2 | 10/2011 | Kim et al. | |
| 8,170,298 B2* | 5/2012 | Li | G06K 9/00308 382/118 |
| 8,194,938 B2* | 6/2012 | Wechsler | G06K 9/627 382/118 |
| 8,199,979 B2 | 6/2012 | Steinberg et al. | |
| 8,212,294 B2 | 7/2012 | Hoke | |
| 8,335,851 B1 | 12/2012 | Vendrow | |
| 8,364,802 B1 | 1/2013 | Keagy et al. | |
| 8,375,456 B2 | 2/2013 | Li | |
| 8,384,714 B2* | 2/2013 | De Aguiar | G06T 13/40 345/420 |
| 8,401,248 B1* | 3/2013 | Moon | G06K 9/00597 382/118 |
| 8,407,472 B2 | 3/2013 | Hao et al. | |
| 8,418,139 B2 | 4/2013 | Dhanakshirur et al. | |
| 8,433,114 B2* | 4/2013 | Reisman | G06K 9/6206 382/128 |
| 8,538,072 B2* | 9/2013 | Kelly | G06F 21/83 382/103 |
| 8,553,037 B2* | 10/2013 | Smith | G06T 13/40 345/473 |
| 8,593,523 B2 | 11/2013 | Wan et al. | |
| 8,680,439 B2 | 3/2014 | Shei et al. | |
| 8,818,034 B2 | 8/2014 | Zhang et al. | |
| 8,839,222 B1 | 9/2014 | Brandwine et al. | |
| 9,082,235 B2* | 7/2015 | Lau | G06K 9/00281 |
| 9,262,152 B1 | 2/2016 | Kurian et al. | |
| 9,495,764 B1* | 11/2016 | Boardman | G06T 7/62 |
| 9,645,808 B1 | 5/2017 | Turpie | |
| 2001/0026634 A1 | 10/2001 | Yamaguchi | |
| 2002/0081003 A1 | 6/2002 | Sobol | |
| 2002/0081032 A1 | 6/2002 | Chen et al. | |
| 2003/0021448 A1 | 1/2003 | Chen et al. | |
| 2003/0108225 A1 | 6/2003 | Li | |
| 2003/0123713 A1 | 7/2003 | Geng | |
| 2004/0042644 A1 | 3/2004 | Yuasa et al. | |
| 2004/0081338 A1 | 4/2004 | Takenaka | |
| 2004/0197014 A1 | 10/2004 | Oohashi | |
| 2005/0105803 A1 | 5/2005 | Ray | |
| 2006/0155777 A1 | 7/2006 | Shih et al. | |
| 2007/0136324 A1 | 6/2007 | Xu et al. | |
| 2008/0066181 A1 | 3/2008 | Haveson et al. | |
| 2009/0193445 A1 | 7/2009 | Thakker | |
| 2010/0008233 A1 | 1/2010 | Ee et al. | |
| 2010/0082316 A1 | 4/2010 | Chawla et al. | |
| 2010/0211908 A1 | 8/2010 | Luk et al. | |
| 2010/0287053 A1 | 11/2010 | Ganong et al. | |
| 2011/0081023 A1 | 4/2011 | Raghuvanshi | |
| 2012/0014560 A1 | 1/2012 | Obrador | |
| 2012/0084655 A1 | 4/2012 | Gallagher et al. | |
| 2012/0243751 A1* | 9/2012 | Zheng | G06K 9/6255 382/118 |
| 2012/0288167 A1* | 11/2012 | Sun | G06K 9/00228 382/118 |
| 2013/0011083 A1 | 1/2013 | Berkovich et al. | |
| 2013/0015946 A1 | 1/2013 | Lau et al. | |
| 2013/0108123 A1 | 5/2013 | Hwang et al. | |
| 2013/0297769 A1 | 11/2013 | Chang et al. | |
| 2013/0305210 A1 | 11/2013 | Sharma et al. | |
| 2013/0311423 A1 | 11/2013 | Price et al. | |
| 2014/0075523 A1 | 3/2014 | Tuomaala | |
| 2014/0087355 A1 | 3/2014 | Henry et al. | |
| 2014/0211065 A1 | 7/2014 | Sudheendra et al. | |
| 2015/0160961 A1 | 6/2015 | Johnson et al. | |
| 2015/0213305 A1 | 7/2015 | Sundstrm | |
| 2015/0234725 A1 | 8/2015 | Cillis et al. | |
| 2015/0302040 A1 | 10/2015 | Amigud et al. | |
| 2020/0210681 A1 | 7/2020 | Chan et al. | |

FOREIGN PATENT DOCUMENTS

| | | |
|---|---|---|
| CN | 101930595 A | 12/2010 |
| CN | 102368194 A | 3/2012 |
| CN | 102722364 A | 10/2012 |
| CN | 102884526 A | 1/2013 |
| GB | 2448050 A | 10/2008 |
| JP | 1347882 B2 | 10/2009 |
| KR | 101240901 B1 | 3/2013 |
| KR | 20140022627 A | 2/2014 |
| WO | 2013008026 A2 | 1/2013 |

OTHER PUBLICATIONS

"Non Final Office Action Issued in U.S. Appl. No. 15/692,494", dated Jul. 19, 2019, 11 Pages.

"Office Action Issued in European Patent Application No. 15721468.5", dated May 24, 2019, 8 Pages.

"Second Office Action and Search Report Issued in Chinese Patent Application No. 201580028549.4", dated Jul. 3, 2019, 10 Pages.

"Second Office Action Issued in Chinese Patent Application No. 201580032034.1", dated Apr. 22, 2019, 13 Pages.

"Second Office Action Issued in Chinese Patent Application No. 201580034192.0", dated Apr. 22, 2019, 10 Pages.

Cordero, Antonio, "Accessing Windows Live Photo Gallery Face API", Retrieved from https://www.acordero.org/2011/06/accessing-windows-live-photo-gallery-face-api/, Jun. 16, 2011, 7 Pages.

Roy, et al., "Face Detection and Its Applications", In Proceedings of the International Journal of Research in Engineering & Advanced Technology, vol. 1, Issue 2, Apr. 2013, 10 Pages.

"First Office Action Issued in Chinese Patent Application No. 201580018659.2", dated Dec. 25, 2018, 19 Pages.

"Office Action Issued in Chinese Patent Application No. 201580018659.2", dated Aug. 23, 2019, 15 Pages.

"Office Action Issued in Chinese Patent Application No. 201580024796.7", dated Aug. 26, 2019, 18 Pages.

"Office Action Issued in Chinese Patent Application No. 201580032034.1", dated Aug. 30, 2019, 6 Pages.

(56) References Cited

OTHER PUBLICATIONS

"Office Action Issued in Chinese Patent Application No. 201580034192.0", dated Sep. 2, 2019, 7 Pages.
"Non Final Office Action Issued in U.S. Appl. No. 16/019,939", dated Sep. 10, 2019, 12 Pages.
"Second Office Action Issued in Chinese Patent Application No. 201580029370.0", dated Sep. 6, 2019, 6 Pages.
"Office Action Issued in European Patent Application No. 15745006.5", dated Dec. 20, 2019, 4 Pages.
"Office Action Issued in Chinese Patent Application No. 201580018659.2", dated Dec. 25, 2019, 11 Pages.
"Office Action Issued in European Patent Application No. 15724882.4", dated Feb. 20, 2020, 6 Pages.
"Office Action Issued in European Patent Application No. 15726780.8", dated Mar. 5, 2020, 7 Pages.
"Office Action Issued in Indian Patent Application No. 201647038515", dated Jun. 18, 2020, 7 Pages.
"Office Action Issued in Indian Patent Application No. 201647042852", dated Jul. 31, 2020, 6 Pages.
"Office Action Issued in Korean Patent Application No. 10-2016-7031483", dated Jan. 11, 2021, 5 Pages.
"Office Action Issued in European Patent Application No. 15726780.8", dated Nov. 24, 2020, 6 Pages.
"Office Action Issued in Indian Patent Application No. 201647038517", dated Nov. 4, 2020, 8 Pages.
"Non Final Office Action Issued in U.S. Appl. No. 16/813,284", dated Nov. 24, 2021, 24 Pages.
Long, et al., "Near Infrared Face Image Quality Assessment System of Video Sequences", In Proceedings of Sixth International Conference on Image and Graphics, Aug. 12, 2011, pp. 275-279.
Nilsson, et al., "Mouth Open or Closed Decision for Frontal Face Images with Given Eye Locations", In Proceedings of Fourth IEEE International Conference on Biometrics: Theory, Applications and Systems, Sep. 27, 2010, 7 Pages.

* cited by examiner

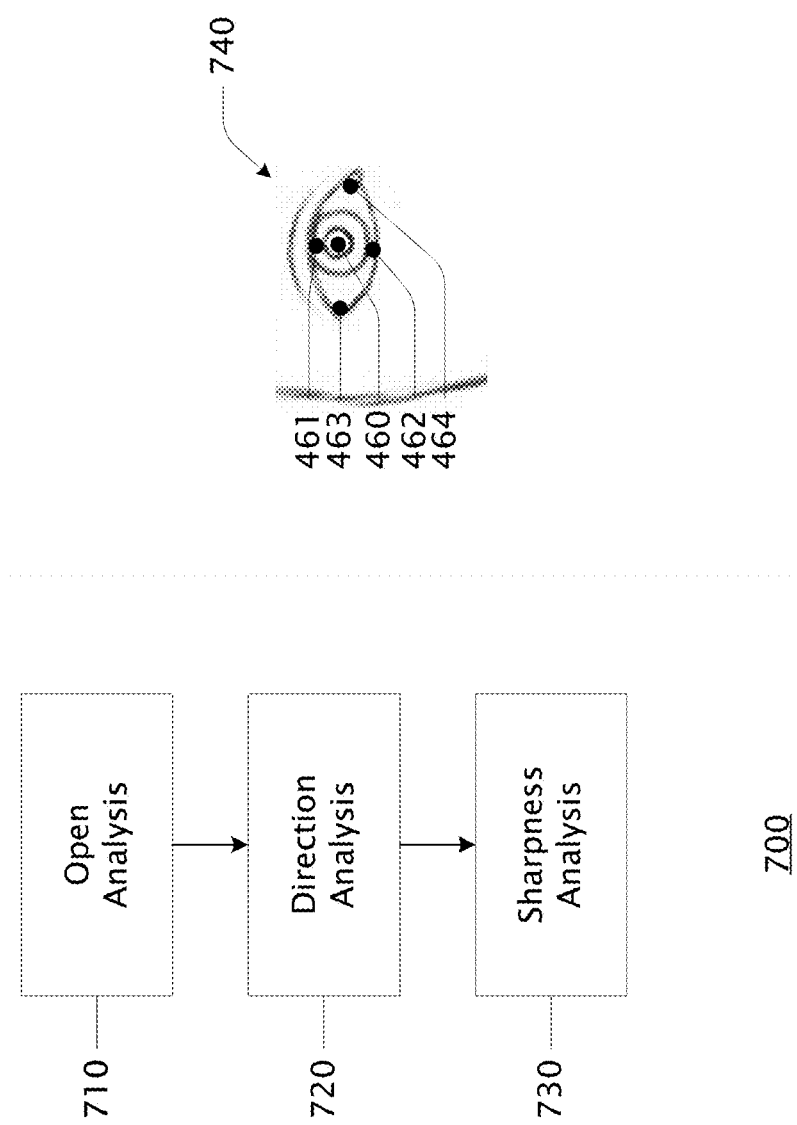

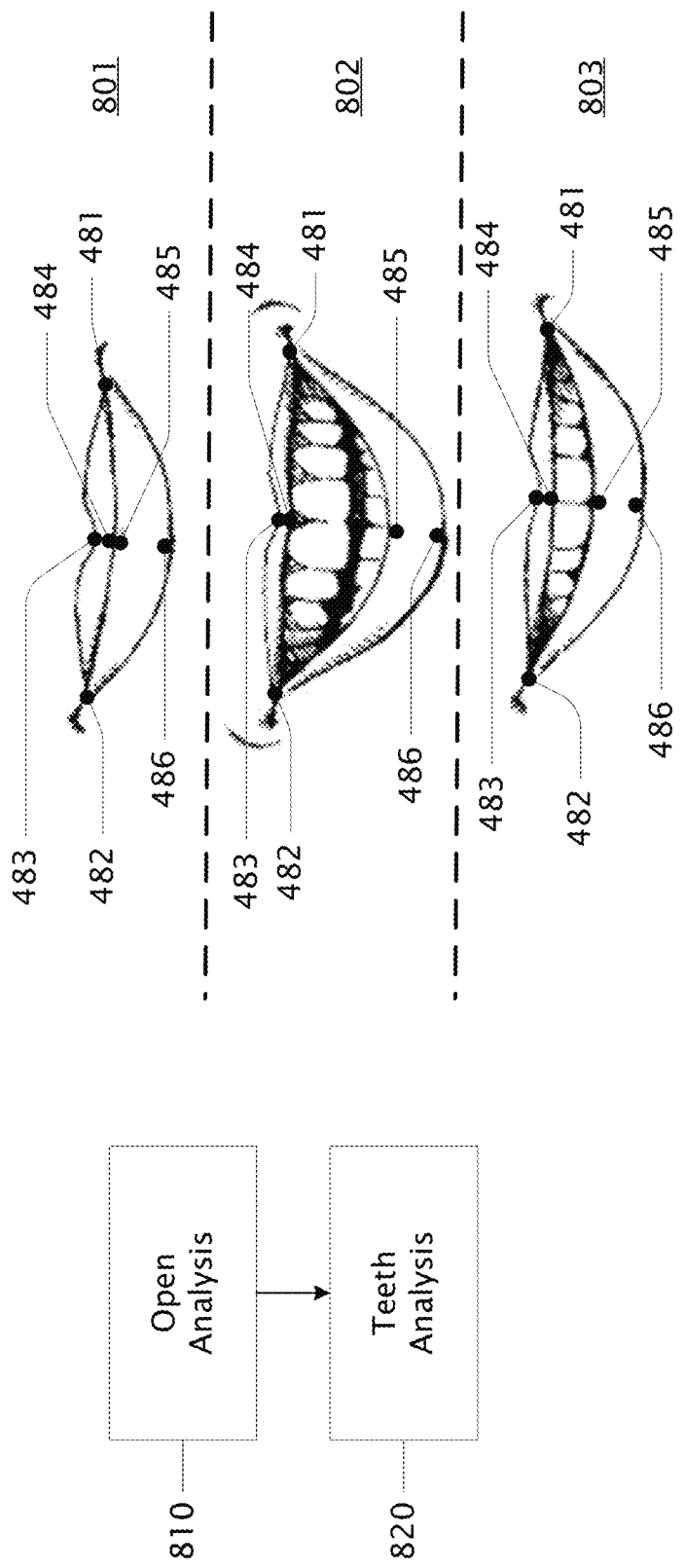

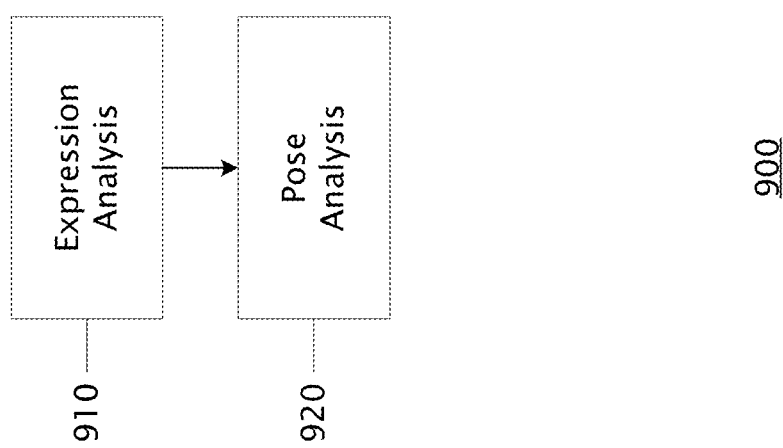

CREATION OF REPRESENTATIVE CONTENT BASED ON FACIAL ANALYSIS

RELATED APPLICATIONS

This Application is a Continuation of and claims benefit from or priority of U.S. patent application Ser. No. 15/497,423, filed Apr. 26, 2017, entitled "CREATION OF REPRESENTATIVE CONTENT BASED ON FACIAL ANALYSIS" which is a continuation of U.S. patent application Ser. No. 14/264,012, filed Apr. 28, 2014, and entitled "CREATION OF REPRESENTATIVE CONTENT BASED ON FACIAL ANALYSIS", now U.S. Pat. No. 9,639,742, issued May 2, 2017, both of which are specifically incorporated by reference for all that they disclose and teach.

BACKGROUND

Thanks to advances in imaging technologies, people take more pictures than ever before. Further, the proliferation of media sharing applications has increased the demand for picture sharing to a greater degree than ever before. Yet the flood of photos, and the need to sort through them to find relevant pictures, has actually increased the time and effort required for sharing pictures. As a result, it is often the case that either pictures that are less than representative of the best pictures, or no pictures at all, end up getting shared.

SUMMARY

The summary provided in this section summarizes one or more partial or complete example embodiments of the invention in order to provide a basic high-level understanding to the reader. This summary is not an extensive description of the invention and it may not identify key elements or aspects of the invention, or delineate the scope of the invention. Its sole purpose is to present various aspects of the invention in a simplified form as a prelude to the detailed description provided below.

The invention encompasses technologies for analyzing various features detected in a face detected in an image. Such features may include at least the eyes, eyebrows, nose, and mouth of a face as reflected in a detected image. Such analyzing may include scoring aspects of these features. Such scores may be weighted. The analysis may be used to determine expressions and/or poses of the face, as well as indicate if the face is smiling, frowning, or neutral. An overall quality score for the face may also be determined and provided based on the aforementioned analysis as well as whether or not the face is near an edge of the image or cut-off in the image. Finally, a face signature may be determined that uniquely identifies the face, at least within the scope of the analyzed features. Such face signatures may be used to detect a similar face in other images. Reference to a face and to eyes, eyebrows, nose, mouth, and other features of the face as used herein typically refers to such as shown in an image as opposed an actual face or its features.

Many of the attendant features will be more readily appreciated as the same become better understood by reference to the detailed description provided below in connection with the accompanying drawings.

DESCRIPTION OF THE DRAWINGS

The detailed description provided below will be better understood when considered in connection with the accompanying drawings, where:

FIG. 7 is a block diagram showing an example eye analysis method and an illustration of an example eye.

FIG. 8 is a block diagram showing an example mouth analysis method and illustrations of example mouths.

FIG. 9 is a block diagram showing an example expression analysis method.

Like-numbered labels in different figures are used to designate similar or identical elements or steps in the accompanying drawings.

DETAILED DESCRIPTION

The detailed description provided in this section, in connection with the accompanying drawings, describes one or more partial or complete example embodiments of the invention, but is not intended to describe all possible embodiments of the invention. This detailed description sets forth various examples of at least some of the technologies, systems, and/or methods invention. However, the same or equivalent technologies, systems, and/or methods may be realized according to examples as well.

Although the examples provided herein are described and illustrated as being implementable in a computing environment, the environment described is provided only as an example and not a limitation. As those skilled in the art will appreciate, the examples disclosed are suitable for implementation in a wide variety of different computing environments.

Figure 1:
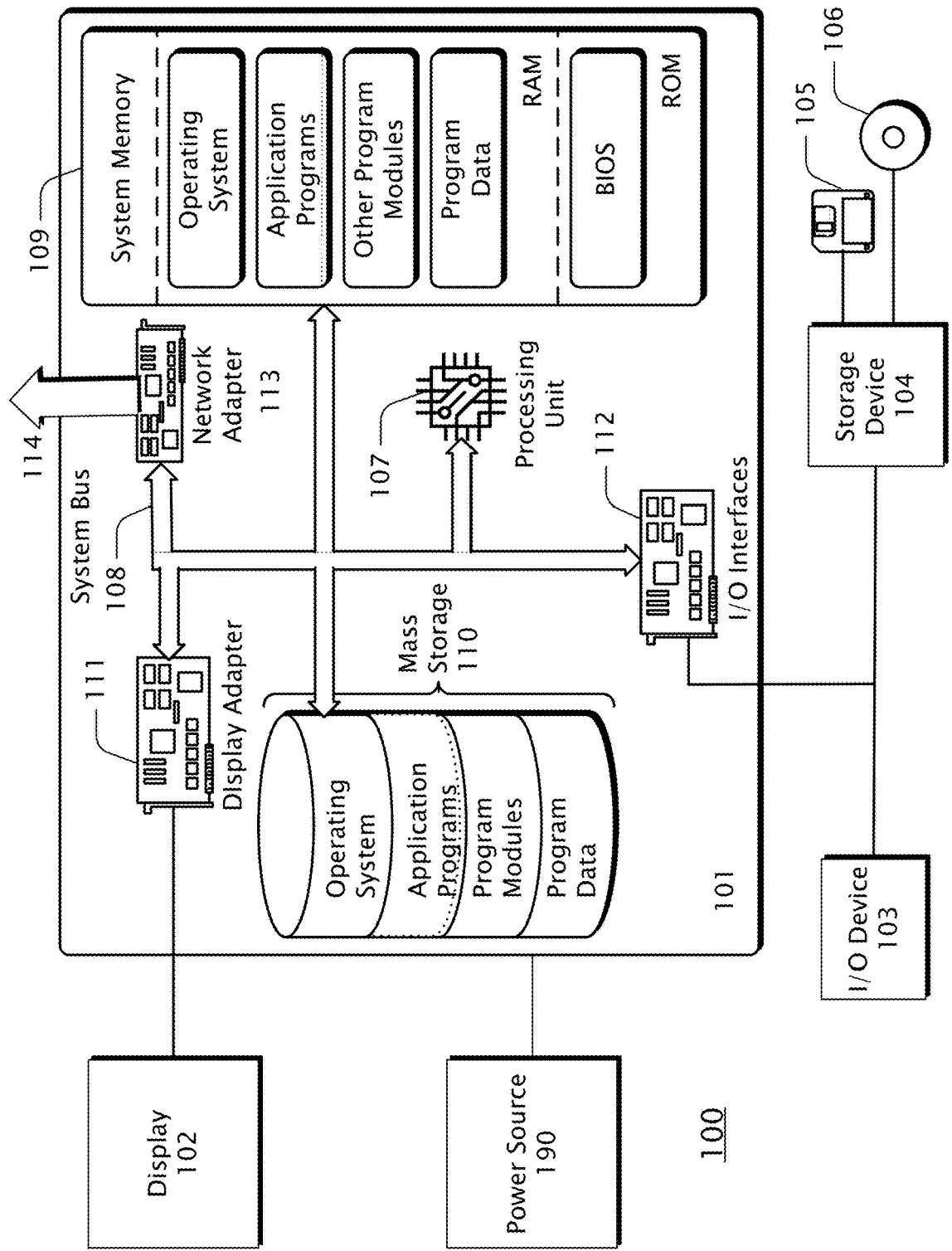
FIG. 1 is a block diagram showing an example computing environment in which the invention described herein may be implemented.

FIG. 1 is a block diagram showing an example computing environment 100 in which the invention described herein may be implemented. A suitable computing environment may be implemented with numerous general purpose or special purpose systems. Examples of well known systems include, but are not limited to, cell phones, personal digital assistants ("PDA"), personal computers ("PC"), hand-held or laptop devices, microprocessor-based systems, multiprocessor systems, systems on a chip ("SOC"), servers, Internet services, workstations, consumer electronic devices, cell phones, set-top boxes, and the like. In all cases, such systems are strictly limited to articles of manufacture and the like.

Computing environment 100 typically includes a general-purpose computing system in the form of a computing device 101 coupled to various components, such as peripheral devices 102, 103, 101 and the like. These may include components such as input devices 103, including voice recognition technologies, touch pads, buttons, keyboards and/or pointing devices, such as a mouse or trackball, that may operate via one or more input/output ("I/O") interfaces 112. The components of computing device 101 may include one or more processors (including central processing units ("CPU"), graphics processing units ("GPU"), microprocessors ("µP"), and the like) 107, system memory 109, and a system bus 108 that typically couples the various components. Processor(s) 107 typically processes or executes various computer-executable instructions and, based on those instructions, controls the operation of computing device 101. This may include the computing device 101 communicating with other electronic and/or computing devices, systems or environments (not shown) via various communications technologies such as a network connection 114 or the like. System bus 108 represents any number of bus structures, including a memory bus or memory controller, a peripheral bus, a serial bus, an accelerated graphics port, a processor or local bus using any of a variety of bus architectures, and the like.

System memory 109 may include computer-readable media in the form of volatile memory, such as random access memory ("RAM"), and/or non-volatile memory, such as read only memory ("ROM") or flash memory ("FLASH"). A basic input/output system ("BIOS") may be stored in non-volatile or the like. System memory 109 typically stores data, computer-executable instructions and/or program modules comprising computer-executable instructions that are immediately accessible to and/or presently operated on by one or more of the processors 107.

Mass storage devices 104 and 110 may be coupled to computing device 101 or incorporated into computing device 101 via coupling to the system bus. Such mass storage devices 104 and 110 may include non-volatile RAM, a magnetic disk drive which reads from and/or writes to a removable, non-volatile magnetic disk (e.g., a "floppy disk") 105, and/or an optical disk drive that reads from and/or writes to a non-volatile optical disk such as a CD ROM, DVD ROM 106. Alternatively, a mass storage device, such as hard disk 110, may include non-removable storage medium. Other mass storage devices may include memory cards, memory sticks, tape storage devices, and the like.

Any number of computer programs, files, data structures, and the like may be stored in mass storage 110, other storage devices 104, 105, 106 and system memory 109 (typically limited by available space) including, by way of example and not limitation, operating systems, application programs, data files, directory structures, computer-executable instructions, and the like.

Output components or devices, such as display device 102, may be coupled to computing device 101, typically via an interface such as a display adapter 111. Output device 102 may be a liquid crystal display ("LCD"). Other example output devices may include printers, audio outputs, voice outputs, cathode ray tube ("CRT") displays, tactile devices or other sensory output mechanisms, or the like. Output devices may enable computing device 101 to interact with human operators or other machines, systems, computing environments, or the like. A user may interface with computing environment 100 via any number of different I/O devices 103 such as a touch pad, buttons, keyboard, mouse, joystick, game pad, data port, and the like. These and other I/O devices may be coupled to processor 107 via I/O interfaces 112 which may be coupled to system bus 108, and/or may be coupled by other interfaces and bus structures, such as a parallel port, game port, universal serial bus ("USB"), fire wire, infrared ("IR") port, and the like.

Computing device 101 may operate in a networked environment via communications connections to one or more remote computing devices through one or more cellular networks, wireless networks, local area networks ("LAN"), wide area networks ("WAN"), storage area networks ("SAN"), the Internet, radio links, optical links and the like. Computing device 101 may be coupled to a network via network adapter 113 or the like, or, alternatively, via a modem, digital subscriber line ("DSL") link, integrated services digital network ("ISDN") link, Internet link, wireless link, or the like.

Communications connection 114, such as a network connection, typically provides a coupling to communications media, such as a network. Communications media typically provide computer-readable and computer-executable instructions, data structures, files, program modules and other data using a modulated data signal, such as a carrier wave or other transport mechanism. The term "modulated data signal" typically means a signal that has one or more of its characteristics set or changed in such a manner as to encode information in the signal. By way of example, and not limitation, communications media may include wired media, such as a wired network or direct-wired connection or the like, and wireless media, such as acoustic, radio frequency, infrared, or other wireless communications mechanisms.

Power source 190, such as a battery or a power supply, typically provides power for portions or all of computing environment 100. In the case of the computing environment 100 being a mobile device or portable device or the like, power source 190 may be a battery. Alternatively, in the case computing environment 100 is a desktop computer or server or the like, power source 190 may be a power supply designed to connect to an alternating current ("AC") source, such as via a wall outlet.

Some mobile devices may not include many of the components described in connection with FIG. 1. For example, an electronic badge may be comprised of a coil of wire along with a simple processing unit 107 or the like, the coil configured to act as power source 190 when in proximity to a card reader device or the like. Such a coil may also be configure to act as an antenna coupled to the processing unit 107 or the like, the coil antenna capable of providing a form of communication between the electronic badge and the card reader device. Such communication may not involve networking, but may alternatively be general or special purpose communications via telemetry, point-to-point, RF, IR, audio, or other means. An electronic card may not include display 102, I/O device 103, or many of the other components described in connection with FIG. 1. Other mobile devices that may not include many of the components described in connection with FIG. 1, by way of example and not limitation, include electronic bracelets, electronic tags, implantable devices, and the like.

Those skilled in the art will realize that storage devices utilized to provide computer-readable and computer-executable instructions and data can be distributed over a network. For example, a remote computer or storage device may store computer-readable and computer-executable instructions in the form of software applications and data. A local computer may access the remote computer or storage device via the network and download part or all of a software application or data and may execute any computer-executable instructions. Alternatively, the local computer may download pieces of the software or data as needed, or distributively process the software by executing some of the instructions at the local computer and some at remote computers and/or devices.

Those skilled in the art will also realize that, by utilizing conventional techniques, all or portions of the software's computer-executable instructions may be carried out by a dedicated electronic circuit such as a digital signal processor ("DSP"), programmable logic array ("PLA"), discrete circuits, and the like. The term "electronic apparatus" may include computing devices or consumer electronic devices comprising any software, firmware or the like, or electronic devices or circuits comprising no software, firmware or the like.

The term "firmware" typically refers to executable instructions, code, data, applications, programs, program modules, or the like maintained in an electronic device such as a ROM. The term "software" generally refers to computer-executable instructions, code, data, applications, programs, program modules, or the like maintained in or on any form or type of computer-readable media that is configured for storing computer-executable instructions or the like in a manner that is accessible to a computing device. The term "computer-readable media" and the like as used herein is strictly limited to one or more apparatus, article of manufacture, or the like that is not a signal or carrier wave per se. The term "computing device" as used in the claims refers to one or more devices such as computing device 101 and encompasses client devices, mobile devices, one or more servers, network services such as an Internet service or corporate network service, and the like, and any combination of such.

Figure 2:
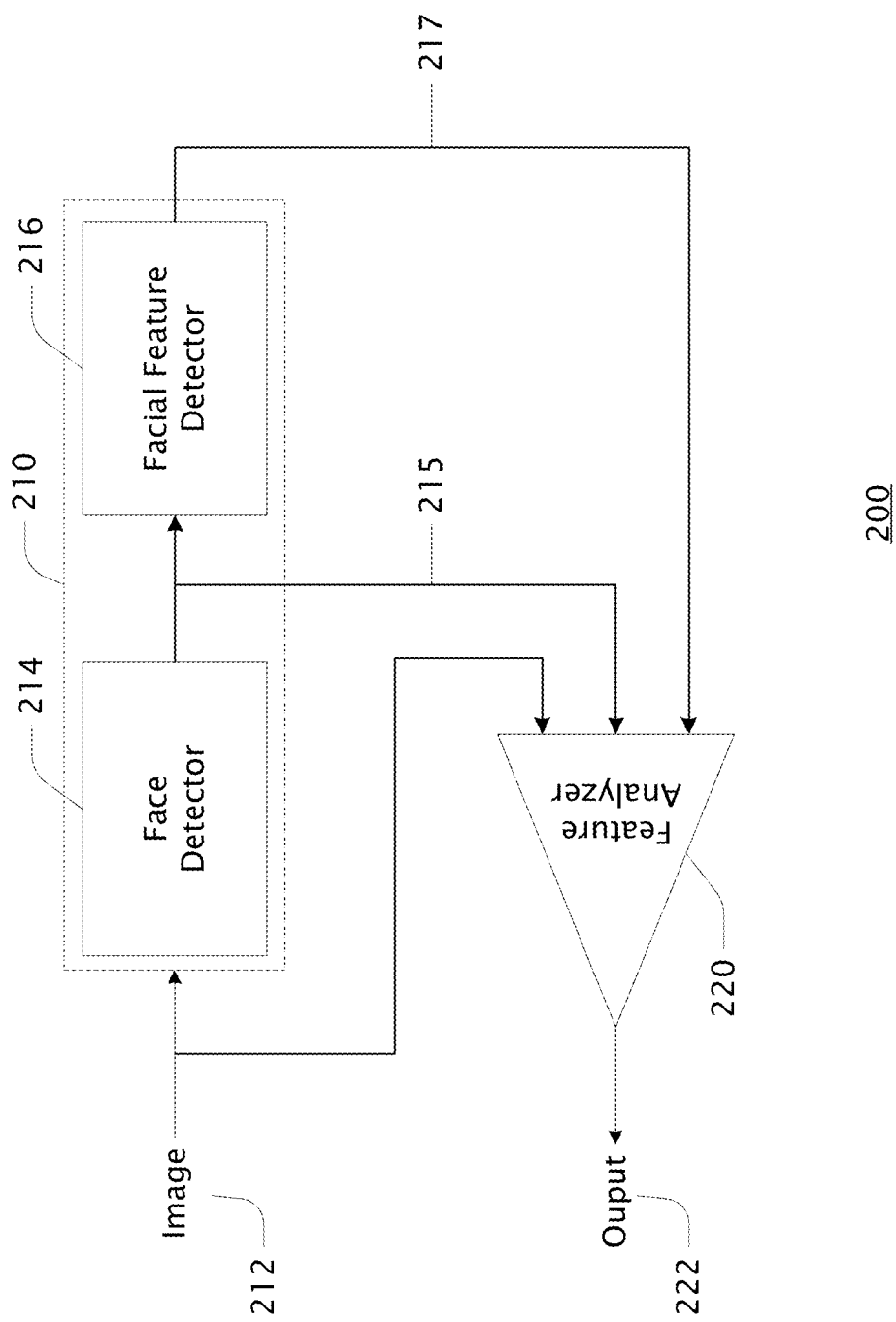
FIG. 2 is a block diagram showing an example system configured for analyzing and scoring a face in an image.

FIG. 2 is a block diagram showing an example system 200 configured for analyzing and scoring a face in an image. The system includes several modules including facial recognition module 210 that accepts input 212, face detector module 214 that may be part of module 210, facial feature detector module 216 that may be part of module 210, and feature analyzer module 220 that accepts inputs 212, 215, and 217 and produces output 222. Each of these modules (including any sub-modules) may be implemented in hardware, firmware, software (e.g., program modules comprising computer-executable instructions), or any combination thereof. Each such module may be implemented on/by one device, such as a computing device, or across multiple such devices. For example, one module may be implemented in a distributed fashion on/by multiple devices such as servers or elements of a network service or the like. Further, each such module (including any sub-modules) may encompass one or more sub-modules or the like, and the modules may be implemented as separate modules, or any two or more may be combined in whole or in part. The division of modules (including any sub-modules) described herein in non-limiting and intended primarily to aid in describing aspects of the invention. The phrase "face in the image" and the like refers not to an actual face in an image, but to an image or representation of a face, actual or otherwise.

In summary, system 200 is configured for analyzing and scoring a face in an image. An image(s) is typically provided by one or more sources as input 212 to the system. Such sources include camera phones, digital cameras, digital video recorders ("DVRs"), computers, digital photo albums, social media applications, image and video streaming web sites, and any other source of digital images. Note that one or more actual images may be input and/or output, or references to images, or any combination of such.

Facial recognition module 210 is a module that accepts an image as input 212, detects one or more faces in the image, and that detects various features in recognized faces. In one example, the functionality of module 210 may be provided in the form of a software development kit ("SDK"). Module 210 may include sub modules such as face detector 214 (e.g., the portion of module 210 that detects faces in an image) and facial feature detector 216 (e.g., the portion of module 210 that detects facial features in an image). Any image provided at input 212 is typically available to both face detector 214 and facial feature detector 216.

Face detector 214 typically provides output 215 in the form of a face identifier that identifies a detected face in image 212. Given multiple detected faces, a unique face identifier is typically provided for face detected. In one example, a face identifier may be a RECT data structure or the like that bounds certain aspects of the face it identifies (e.g., see example rectangle 410 in FIG. 4). Such a RECT data structure may indicate a position in the image of the face it identifies, and/or may indicate a size or relative size of the identified face in the image. Any face identifier(s) that are output 215 by face detector 214 may be accepted as input by facial feature detector 216 and/or by feature analyzer module 220 to uniquely identify a corresponding face(s) in the image. Any suitable techniques may be used by face detector 214 to detect faces in input image 212.

Facial feature detector 216 typically accepts an image and a face identifier(s) of any face(s) detected in the image. Module 216 typically provides output 217 in the form of a set of facial feature descriptors that describe facial features detected in a face corresponding to a face identifier. Given multiple face identifiers as input, a corresponding set of facial feature descriptors is typically provided for each face identifier. In one example, the set of facial feature descriptors may be in the form of coordinates for each detected facial features, such as described in connection with FIG. 4. Any suitable techniques may be used by facial feature detector 216 to detect facial features in faces in input image 212.

Feature analyzer 220 typically accepts an image, a face identifier(s) of any face(s) detected in the image, and a corresponding set of facial feature descriptors for each face detected. Module 220 typically provides output 222 in the form of face information for each face detected. In one example, such face information may include, for each face detected, the face identifier of the face, the face's set of facial feature descriptors, a quality score of the face, a unique signature for the face, an indication of an expression of the face, and indication of a pose of the face, and/or additional analysis results such as described herein below. Such indications may be provided in the form of a score or the like, or in any other form. Such a face signature may be used to detect, based at least on analyzed facial features, similar faces in other images, where such similar faces typically belong to the same person, closely-related persons, or similar-looking persons.

Figure 3:
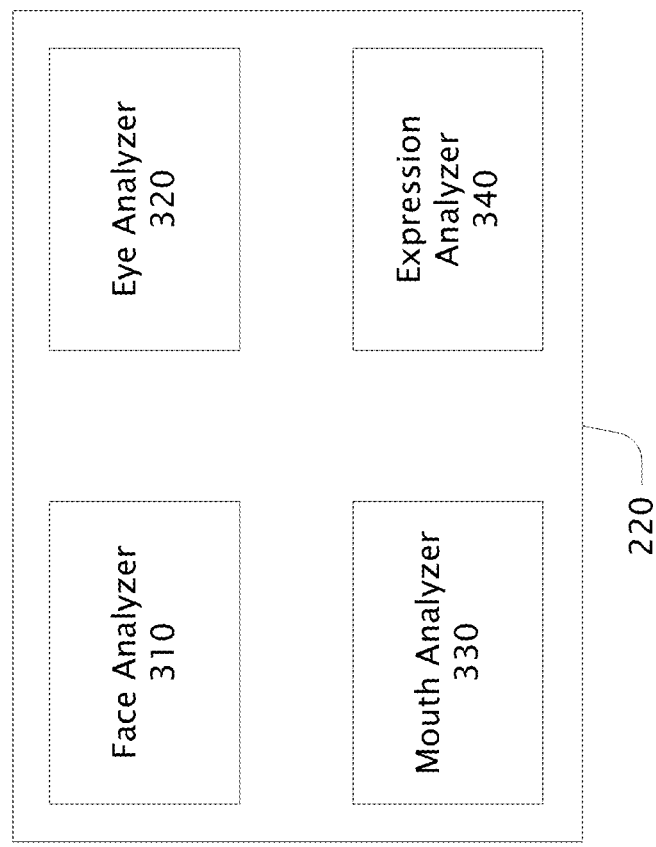
FIG. 3 is a block diagram showing an example feature analyzer that includes sub modules such as face analyzer, eye analyzer, mouth analyzer, and expression analyzer.

FIG. 3 is a block diagram showing an example feature analyzer 220 that includes sub modules such as face analyzer 310, eye analyzer 320, mouth analyzer 330, and expression analyzer 340. Each such sub-module may accept as input an image, a face identifier for any face(s) detected in the image, and a set of facial feature descriptors for each face detected in the image. The following discusses each sub-module from the perspective of a single detected face in an image, but the functionality of each sub-module may also apply to any number of faces detected in the image.

Face analyzer 310 may analyze one or more aspects of a face. For example, module 310 may analyze the input to determine a location of the face in the image, a degree to which the face is cut-off in the image, a degree of sharpness of the face, and a confidence level that a detected face actually represents a face. Examples of methods for the foregoing are provided below in connection with FIG. 6 below.

Eye analyzer 320 may analyze one or more aspects of an eye(s) in the face. For example, module 320 may analyze the input to determine a degree to which an eye is open, the direction an eye is looking, and/or a degree of sharpness of an eye in the image. Examples of methods for the foregoing are provided below in connection with FIG. 7.

Mouth analyzer 330 may analyze one or more aspects of a mouth in the face. For example, module 330 may analyze the input to determine a degree to which the mouth is open, and a degree to which teeth are visible in the mouth. Examples of methods for the foregoing are provided below in connection with FIG. 8.

Expression analyzer 340 may analyze one or more aspects of the face, the eyes, and the mouth in the face. For example, module 340 may analyze the input to determine an expression on and/or a pose of the face. Examples of methods for the foregoing are provided below in connection with FIG. 9.

Figure 4:
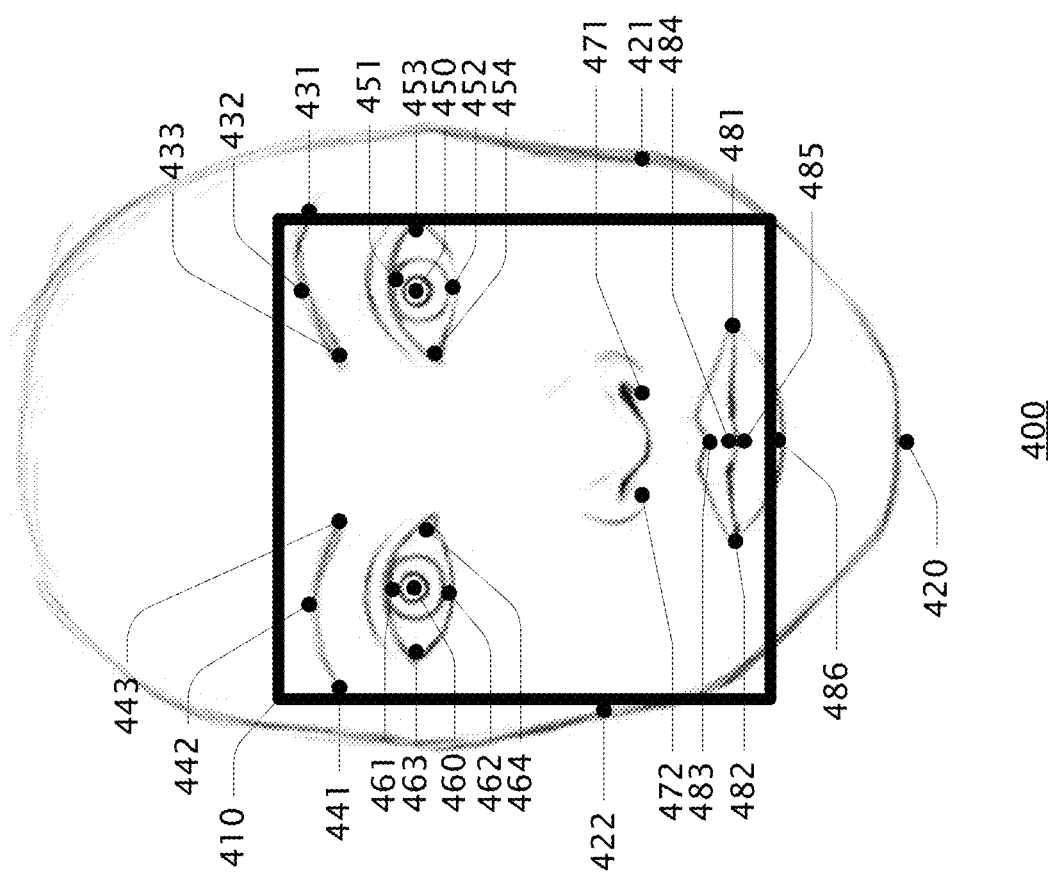
FIG. 4 is a diagram showing an example face with certain aspects of the face bounded by a rectangle that is associated with a face identifier that uniquely identifies the face in the image.

FIG. 4 is a diagram showing an example face with certain aspects of the face bounded by a rectangle 410 that is associated with a face identifier that uniquely identifies the face in the image. The example face in FIG. 4 is also marked with example points indicating coordinates of various detected facial features of the face. Such coordinates may be identified by a set of facial feature descriptors and may be relative to a reference point of rectangle 410, a reference point of the image that includes the face, or to some other reference point. Such face identifiers and sets of facial feature descriptors may be provided by a module such as facial recognition module 210.

In one example, features on the face may be detected and indicated with coordinate points such as a chin point 420 and face side points 421 and 422. In addition, coordinate points 431, 432, and 433 may indicate a detected left eye brow, coordinate points 441, 442, and 443 may indicated a detected right eye brow, and coordinate points 471 and 472 may indicate a detected nose.

In the example, the left eye of the face may be detected and indicated with coordinate points 451-454, with coordinate point 450 indicating a direction the eye is looking. The right eye of the face may be detected and indicated with coordinate points 461-464, with coordinate point 460 indicating a direction the eye is looking. The phrases "direction the eye is looking", "eye direction", and the like generally refer to the direction the eye is pointing or aimed. Further, the mouth of the face may be detected and indicated with coordinate points 481-486.

Figure 5:
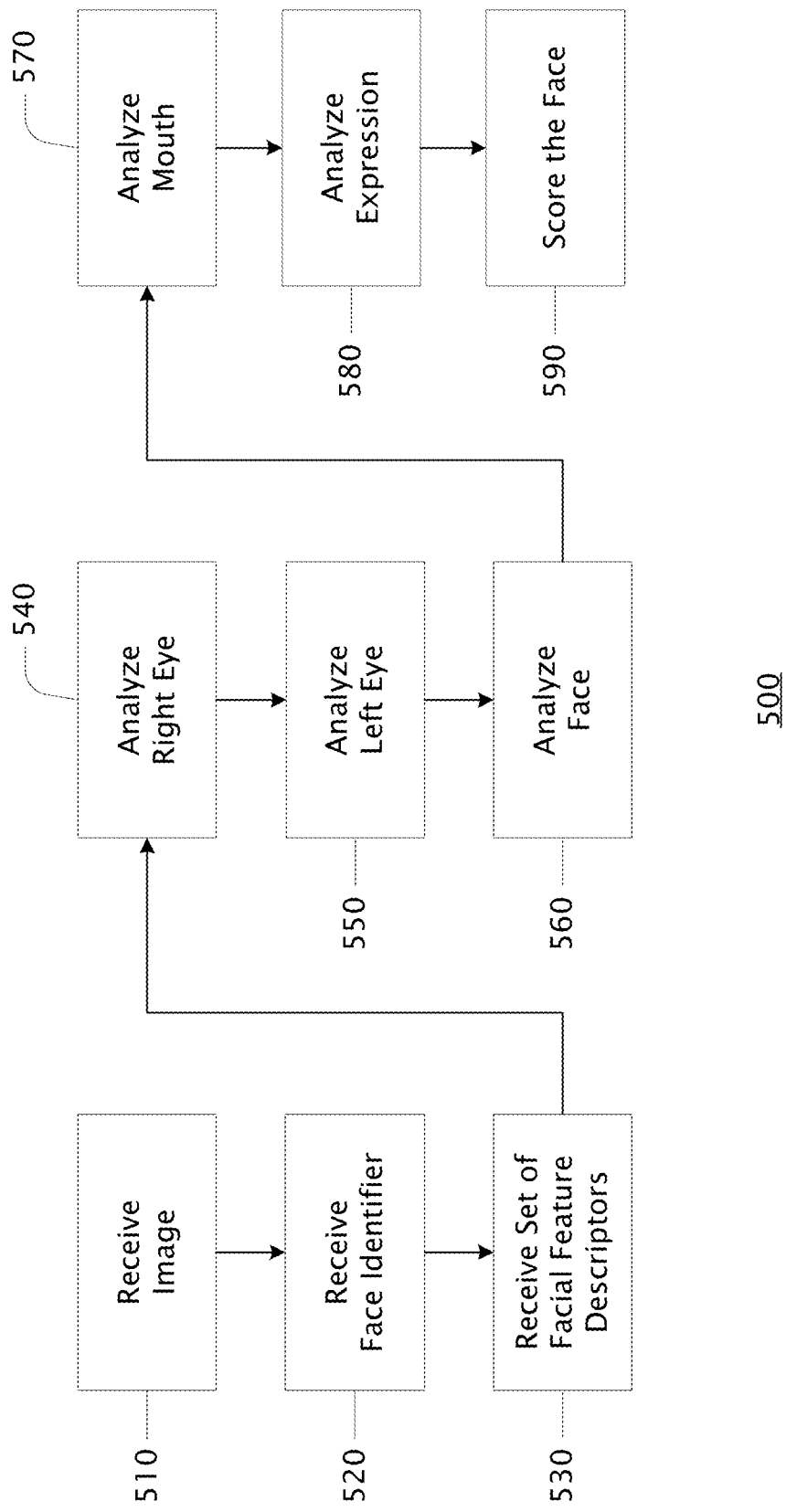
FIG. 5 is a block diagram showing an example method for analyzing and scoring a face in an image.

FIG. 5 is a block diagram showing an example method 500 for analyzing and scoring a face in an image. Such a method may be performed by feature analyzer 220 or the like. In one example, various inputs are received such as an image (at block 510), a face identifier that identifies a face detected in the image (at block 520), and a set of facial feature descriptors that describe facial features detected in a face corresponding to a face identifier (at block 530). One or more of the foregoing inputs are then typically used in analyzing and scoring various aspects of the face. The various inputs may be received separately or in any combination. One or more of these inputs may be used in the various analysis steps performed in method 500. Further, in one example, at least steps 540, 550, 560, and 570 may be performed in any order as opposed to the order shown.

For example, block 540 of method 500 typically indicates analyzing aspects of the right eye of the face, and block 550 of method 500 typically indicates analyzing aspects of the left eye of the face. Examples of eye analysis are provided below in connection with FIG. 7 below. Block 560 of method 500 typically indicates analyzing aspects of the face. Examples of face analysis are provided below in connection with FIG. 6 below. Block 570 of method 500 typically indicates analyzing aspects of the mouth of the face. Examples of mouth analysis are provided below in connection with FIG. 8 below. Block 580 of method 500 typically indicates analyzing the expressions and the pose of the face. Examples of expression analysis are provided below in connection with FIG. 9 below.

Block 590 of method 500 typically indicates calculating a score for the face. Such a face score may be an overall quality score for the face that is based on one or more of the analysis steps of method 500. In one example, the score may be a value between zero and one. In other examples, the score may be represented by a value within a continuous range, or by a quantization such as high, medium, or low, or the like. In one example, the face score may represent an overall measure of the quality of the face in the image, and may be based on a combination of analyzed aspects such as face sharpness, face expression, face pose, and/or the state of the face's eyes and mouth. Such a score may be provided as output 222 in response to image input 212.

Figure 6:
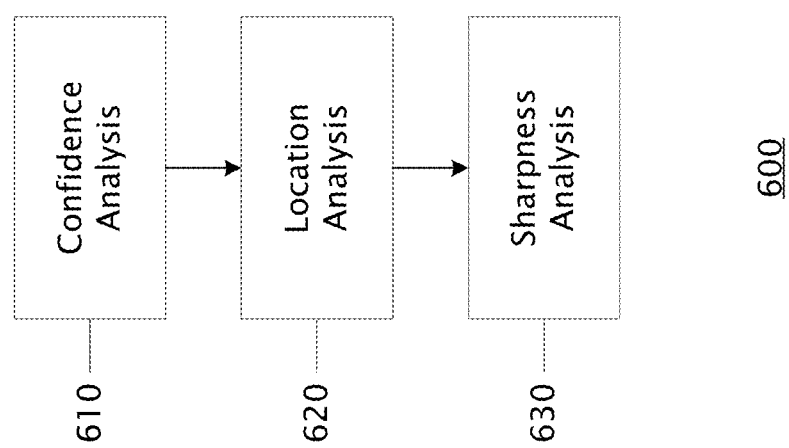
FIG. 6 is a block diagram showing an example face analysis method.

FIG. 6 is a block diagram showing an example face analysis method 600. Such a method may be performed by face analyzer 310 or the like. In one example, method 600 includes confidence analysis 610, location analysis 620, and sharpness analysis 630. In one example, various inputs to method 600 are provided, such as an image, a face identifier that identifies a face detected in the image, and a set of facial feature descriptors that describe facial features detected in a face corresponding to a face identifier. One or more of the foregoing inputs are then typically used in the face analysis.

Block 610 typically indicates presenting or determining a confidence level that a detected face represents an actual face. Such a level may be received as part of the input, or may be determined based on data received as part of the input. In the latter case, the level may be based on the face identifier and the set of facial feature descriptors received as input. For example, a face indicator that indicates a proportionate face size relative to the image and/or a more complete and consistent set of facial feature descriptors tend to indicate a higher confidence, while an disproportionate face size and a less complete and consistent set tend to indicate a lower confidence.

A confidence score may be assigned to the face that represents the confidence level. Such a confidence score may be weighted, and may be represented by a real number between zero and one, a value within some other range, and/or by a quantization such as high/medium/low, and/or the like.

Block 620 typically indicates determining a location of the face in the image. Based on this location, and the size of the face according to the face identifier, a proximity of the face to an edge of the image may also be determined. The proximity of the face to an edge of the image may be compared to an unacceptable proximity range resulting in a location score for the face. Such a proximity range may be specified by a constant or by a variable that may be pre-set and/or definable by a user, a machine learning system, or otherwise. In one example, a lower location score may be assigned if the face is located at least in part within the unacceptable proximity range than if the face is located entirely outside the range. Such a proximity range may be specified by a constant or by a variable that may be pre-set and/or definable by a user, a machine learning system, or otherwise.

Such a face location score may be weighted, and may be represented by a real number between zero and one, by a value within some other continuous range, and/or by a quantization such as acceptable or unacceptable, or high, medium, or low, or the like. A user may be a person or a system of any type.

Further, based on the face location and/or the facial feature descriptors of the face, block 620 may include determining if the face is cut-off at the edge of the image. The term "cut-off" as used herein generally refers to some portion of the face being located at an edge of the image such that a portion of the face is not shown in the image (i.e., the cut-off portion). A certain cut-off range may be defined (such as up to a certain percentage or the like of a face that is cut-off). Such a cut-off range may be specified by a constant or by a variable that may be pre-set and/or definable by a user, a machine learning system, or otherwise.

A cut-off score may be assigned to the face that represents the degree to which the face is cut off. Such a face cut-off score may be weighted, and may be represented by a real number between zero and one, by a percentage, by a value within some other range, and/or by a quantization such as acceptable/unacceptable, cut off/not cut off, and/or the like.

Block 630 typically indicates determining a degree of sharpness of the face. In one example, the degree of sharpness may be based on pixel contrast of lines of the face, where greater contrast across fewer pixels typically indicates a greater degree of face sharpness in contrast to lesser contrast across more pixels that typically indicates a lesser degree of face sharpness.

A sharpness score may be assigned to the face that represents the degree of sharpness. Such a face sharpness score may be weighted, and may be represented by a real number between zero and one, by a value within some other range, and/or by a quantization such as acceptable/unacceptable, high/medium/low, and/or the like.

Block 640 typically indicates determining a face color. In one example, the color of the face may be determined from an area of the face selected based on the facial features, such as areas proximate the eyes and/or nose. In one example, a area proximate the eyes and/or nose is selected and a dominant color in that area is determined. If the determined color corresponds to an expected color, then the face color may be assigned a higher score than if the determined color does not correspond to an expected color. Such a face color score may indicate a degree of correspondence to the expected color. Further, a set of expected colors may be provided and used in score the determined face color.

Such a face color score may be weighted, and may be represented by a real number between zero and one, by a value within some other range, and/or by a quantization such as acceptable/unacceptable, estimated ethnicities based on the determined color, color descriptions (e.g., black/white, etc), and/or the like.

FIG. 7 is a block diagram showing an example eye analysis method 700 and an illustration of an example eye 740. Such a method may be performed by face analyzer 310 or the like. In one example, method 700 includes open analysis 710, direction analysis 720, and sharpness analysis 730. In one example, various inputs to method 700 are provided, such as an image, a face identifier that identifies a face detected in the image, and a set of facial feature descriptors that describe facial features detected in the face corresponding to a face identifier. One or more of the foregoing inputs are then typically used in the face analysis.

Block 710 typically indicates determining an open-closed state of an eye in the detected face. Such a state may be determined for the right eye, the left eye or both. The method may be performed in substantially the same manner regardless of the particular eye being analyzed. In one example, the determination is made based on eye coordinate points, such as points 461-464 shown for example eye 740. In this example, points 463 and 464 typically indicate the broadest detected horizontal edges of the eye, and may be used to determine the eye's width as it appears in the image. Points 461 and 462 typically indicate the broadest detected vertical edges of the eye, and may be used to determine the eye's height as it appears in the image. A ratio of the height to the width, or the width to the height, may indicate the open-closed state of the eye.

An eye open-closed score may be assigned to the eye and/or the face that represents the eye's open-closed state. Such an eye open-closed score may be weighted, and may be represented by a real number between zero and one, a ratio, a value within some other range, an opened and/or closed percentage, and/or by a quantization such as open/closed, and/or the like.

In some situations, such as when the face is turned to one side, only one of the horizontal edges of the eye may be detectable in the face. In such a situation, information that indicates a degree to which the face is turned, along with the available eye coordinate points, may be used to estimate the eye's width. Such information may be available as part of the input, and/or may be available as output from expression analyzer 340 or from some other module. Such an estimated width may be used as the determined eye's width in method 710.

Block 720 typically indicates determining a direction an eye is looking. Such a direction may be determined for the right eye, the left eye or both. The method may be performed in substantially the same manner regardless of the particular eye being analyzed. In order to determine the direction an eye is looking, the open-closed state of the eye may need to be sufficiently open to enable detecting eye coordinate point 460. The pose of the face may also need to be sufficient to enable detecting eye coordinate point 460.

In one example, the determination is made based on eye coordinate points, such as points 460-464 shown for example eye 740. In this example, a location of point 460 in relation to points 462-463 and/or to points 463-464 may be used in determining the direction the eye is looking. For example, if point 460 is located substantially equidistant from each of points 461-464, and if points 461 and 462 are located substantially equidistant from points 463 and 464, then the direction the eye is looking may be determined to be substantially forward. In this example, forward may also be toward the camera that captured the image.

Continuing the previous example, if point 460 is located to the right of points 463-464, then the direction the eye is looking may be determined to be to the right. If point 460 is located to the left of points 463-464, then the direction the eye is looking may be determined to be to the left. If point 460 is located above points 463-464, then the direction the eye is looking may be determined to be upward. If point 460 is located below points 463-464, then the direction the eye is looking may be determined to be downward.

An eye direction score may be assigned to the eye and/or the face that represents the eye direction. Such an eye direction score may be weighted, and may be represented by a real number between zero and one, an angle, a value in degrees, a value within some other range, and/or by a quantization such as toward the camera/not toward the camera, toward a subject of the image/not toward a subject of the image, forward/not forward, up/down, right/left, and/or the like.

Block 730 typically indicates determining a degree of sharpness of an eye in the detected face. Such a degree of sharpness may be determined for the right eye, the left eye or both. The method may be performed in substantially the same manner regardless of the particular eye being analyzed. In one example, the degree of sharpness may be based on pixel contrast of lines of the eye and/or around the eye, where greater contrast across fewer pixels typically indicates a greater degree of eye sharpness in contrast to lesser contrast across more pixels that typically indicates a lesser degree of eye sharpness.

A sharpness score may be assigned to the eye that represents the degree of sharpness. Such an eye sharpness score may be weighted, and may be represented by a real number between zero and one, by a value within some other continuous range, and/or by a quantization such as acceptable or unacceptable, or high, medium, or low, or the like.

FIG. 8 is a block diagram showing an example mouth analysis method 800 and illustrations of example mouths 801, 802, and 803. Such a method may be performed by mouth analyzer 330 or the like. In one example, method 800 includes open analysis 810 and teeth analysis 820. In one example, various inputs to method 800 are provided, such as an image, a face identifier that identifies a face detected in the image, and a set of facial feature descriptors that describe facial features detected in the face corresponding to a face identifier. One or more of the foregoing inputs are then typically used in the mouth analysis.

Block 810 typically indicates determining an open-closed state of a mouth in the detected face. In one example, the determination is made based on mouth coordinate points, such as points 481-486 shown for example mouths 801, 802, and 803. In this example, points 481 and 482 typically indicate the broadest detected horizontal edges of the mouth, and may be used to determine the mouth's width as it appears in the image. Points 483 and 484 typically indicate the top of the upper lip and the bottom of the upper lip respectively. Points 485 and 486 typically indicate the top of the lower lip and the bottom of the lower lip respectively. Points 483 and 486 typically indicate the broadest detected vertical edges of the mouth, and may be used to determine the mouth's height as it appears in the image. The mouth's height and width may be used to determine an area of the mouth on the face, or an approximation or estimation thereof.

Further, points 484 and 485 may be used to determine a distance between the bottom of the upper lip and the top of the lower lip, where such a distance may indicate the open-closed state of the mouth. A ratio of the height to the distance, or the distance to the height, may indicate the open-closed state of the mouth.

A mouth open-closed score may be assigned to the mouth and/or the face that represents the mouth's open-closed state. Such a mouth open-closed score may be weighted, and may be represented by a real number between zero and one, a ratio, a value within some other range, an opened and/or closed percentage, and/or by a quantization such as open/closed, and/or the like.

In some situations, such as when the face is turned to one side, only one of the horizontal edges of the mouth may be detectable in the face. In such a situation, information that indicates a degree to which the mouth is turned, along with the available mouth coordinate points, may be used to estimate the mouth's width. Such information may be available as part of the input, and/or may be available as output from expression analyzer 340 or from some other module. Such an estimated width may be used as the determined mouth's width in method 810.

Block 820 typically indicates determining whether or not teeth are visible in the mouth, or determining an amount of the mouth area in which teeth are visible. Recognition of teeth is typically based on the presence of a pale color in an area of the mouth where teeth may typically be anticipated. In one example, this area—termed herein the "teeth area"—is defined as the portion of an open mouth between points 481 and 482 and between points 484 and 485, not including the lips of the mouth, or an approximation or estimation thereof.

If the open-closed state of the mouth is determined to be closed, then it may also be determined that no teeth are visible, such as in example 801. If the mouth is determined to be open, and a pale color is detected in at least a portion of the teeth area of the mouth, then it may be determined that teeth are visible, such as in examples 802 and 803. A comparison between the mouth area and the portion of the teeth area in which teeth are detected may be made to determine a measure of visible teeth in the mouth.

A teeth visible score may be assigned to the mouth and/or face that represents the determined measure of visible teeth. Such a teeth visible score may be weighted, and may be represented by a real number between zero and one, by a value within some other range, and/or by a quantization such as visible/not visible, and/or the like.

FIG. 9 is a block diagram showing an example expression analysis method 900. Such a method may be performed by expression analyzer 330 or the like. In one example, method 900 includes expression analysis 810 and/or pose analysis 820. In one example, various inputs to method 900 are provided, such as an image, a face identifier that identifies a face detected in the image, and a set of facial feature descriptors that describe facial features detected in the face corresponding to a face identifier. One or more of the foregoing inputs are then typically used in the expression and/or pose analysis.

Block 910 typically indicates determining an expression(s) of the detected face. In one example, such determined expressions may be selected from a set comprising smiling, frowning, neutral, and other. In this example, determining such expressions may largely be based on the mouth and mouth analysis 800. For example, the location of points 481 and 482 relative to point 485 may be used to select one of the expressions in the set. Smiling may be selected if points 481 and 482 are located above point 485. Frowning may be selected if points 481 and 482 are located below point 485. Neutral may be selected if points 481 and 482 are located substantially in-line with point 485. Other may be selected for an arrangement of the points that is inconsistent with any of those previously described.

An expression score may be assigned to the face that represents the face's expression. Such an expression score may be weighted, and may be represented by a real number between zero and one, a value within some other range, and/or by a quantization such as smiling/frowning/neutral/other, and/or the like.

Block 920 typically indicates determining a pose(s) of the detected face. Face poses may be determined based on information such as relative positions of the eyes, nose, mouth, eyebrows, and the size of the face. Further, information describing or indicating the orientation of the face may be received or determined. All such information (received and/or determined) may be used to determine and indicate various poses of the face, such as forward or other facing, tilted up or down, right or left, looking at the camera that captured the image, looking at a subject in the image, etc. One or more indications of determined and/or received poses may be provided. Further, a pose score may be assigned to the face that represents the face's pose and/or pose quality. Such a pose score may be weighted, and may be represented by a real number between zero and one, a value within some other range, and/or by a quantization such as tilted right/left and/or up/down, and/or the like.

In view of the many possible embodiments to which the invention and the forgoing examples may be applied, it should be recognized that the examples described herein are meant to be illustrative only and should not be taken as limiting the scope of the present invention. Therefore, the invention as described herein contemplates all such embodiments as may come within the scope of the following claims and any equivalents thereto.

The invention claimed is:

1. A method performed on a computing device, the method comprising:
   detecting a first face in a first image;
   analyzing, by the computing device, features of the detected first face to generate a set of facial feature descriptors, wherein individual facial feature descriptors describe individual features that differ from features described by other facial feature descriptors in the set of facial feature descriptors, the set of facial feature descriptors comprising multiple facial feature descriptors that describe multiple features of the detected first face;
   generating, by the computing device a face signature based on multiple distinct inputs, comprising: (1) individual ones of the multiple facial feature descriptors from the set of facial feature descriptors that were generated by the analyzing the features of the first face and (2) from the first image, corresponding individual ones of the multiple features of the first face that was detected in the first image by the detecting; and
   identifying a face in a second image as being similar to the first face, at least within a scope of the analyzed features, based on the generated face signature.

2. The method of claim 1 where the generated face signature is sufficient to identify faces in other images that are of a same person as the detected face.

3. The method of claim 1 further comprising generating, by the computing device based on the analyzed features of the detected face, a quality score of the detected face.

4. The method of claim 3 where the quality score is influenced based on whether or not the detected face is located near an edge of the image.

5. The method of claim 3 where the quality score is influenced based on whether or not the detected face is cut off in the image.

6. The method of claim 1 further comprising generating, by the computing device based on the analyzed features of the detected face, an expression of the detected face.

7. The method of claim 1 further comprising generating, by the computing device based on the analyzed features of the detected face, a pose of the detected face.

8. A computing device comprising:
   a processor;
   memory coupled to the processor;
   a program module that is stored in the memory and that, based on execution by the processor, configures the computing device to perform actions comprising:
   detecting a first face in a first image;
   analyzing, by the computing device, features of the detected first face to generate a set of facial feature descriptors, wherein individual facial feature descriptors describe individual features that differs from features described by other facial feature descriptors in the set of facial feature descriptors, the set of facial feature descriptors comprising multiple facial feature descriptors that describe multiple features of the detected first face
   generating, by the computing device, a face signature based on multiple distinct inputs, comprising: (1) individual ones of the multiple facial feature descriptors from the set of facial feature descriptors that were generated by the analyzing the features of the first face and (2) from the first image, corresponding individual ones of the multiple features of the first face that was detected in the first image by the detecting; and
   identifying a face in a second image as being similar to the first face at least within a scope of the analyzed features, based on the generated face signature.

9. The computing device of claim 8 where the generated face signature is sufficient to identify faces in other images that are of a same person as the detected face.

10. The computing device of claim 8, the actions further comprising generating, by the computing device based on the analyzed features of the detected face, a quality score of the detected face.

11. The computing device of claim 10 where the quality score is influenced based on whether or not the detected face is located near an edge of the image.

12. The computing device of claim 10 where the quality score is influenced based on whether or not the detected face is cut off in the image.

13. The computing device of claim 8, the actions further comprising generating, by the computing device based on the analyzed features of the detected face, an expression of the detected face.

14. The computing device of claim 8, the actions further comprising generating, by the computing device based on the analyzed features of the detected face, a pose of the detected face.

15. At least one computer-readable media storing computer-executable instructions that, when executed by a computing device, cause the computing device to perform actions comprising:
    detecting a first face in a first image;
    analyzing, by the computing device, features of the detected first face to generate a set of facial feature descriptors, wherein individual facial feature descriptors describe individual features that differ from features described by other facial feature descriptors in the set of facial feature descriptors, the set of facial feature descriptors comprising multiple facial feature descriptors that describe multiple features of the detected first face;
    generating, by the computing device a face signature based on multiple distinct inputs, comprising: (1) individual ones of the multiple facial feature descriptors from the set of facial feature descriptors that were generated by the analyzing the features of the first face and (2) from the first image, corresponding individual ones of the multiple features of the first face that was detected in the first image by the detecting; and
    identifying a face in a second image as being similar to the first face, at least within a scope of the analyzed features, based on the generated face signature.

16. The at least one computer-readable media of claim 15 where the generated face signature is sufficient to identify faces in other images that are of a same person as the detected face.

17. The at least one computer-readable media of claim 15, the actions further comprising generating, by the computing device based on the analyzed features of the detected face, a quality score of the detected face.

18. The at least one computer-readable media of claim 17 where the quality score is influenced based on whether or not the detected face is located near an edge of the image, or where the quality score is influenced based on whether or not the detected face is cut off in the image.

19. The at least one computer-readable media of claim 17, the actions further comprising generating, by the computing device based on the analyzed features of the detected face, an expression of the detected face.

20. The at least one computer-readable media of claim 15, the actions further comprising generating, by the computing device based on the analyzed features of the detected face, a pose of the detected face.

\* \* \* \* \*